United States Patent
Tanaka et al.

(10) Patent No.: US 8,124,715 B2
(45) Date of Patent: Feb. 28, 2012

(54) ISOCYANURIC RING-CONTAINING POLYSILOXANE HAVING VINYL GROUPS AT THE TERMINALS

(75) Inventors: Hayato Tanaka, Annaka (JP); Tsutomu Kashiwagi, Annaka (JP); Toshio Shiobara, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/938,639

(22) Filed: Nov. 3, 2010

(65) Prior Publication Data

US 2011/0105713 A1 May 5, 2011

(30) Foreign Application Priority Data

Nov. 4, 2009 (JP) .................................. 2009-253318
Oct. 5, 2010 (JP) .................................. 2010-225825

(51) Int. Cl.
*C08G 77/20* (2006.01)
(52) U.S. Cl. .......................................... 528/32; 528/33
(58) Field of Classification Search ................ 528/32, 528/33
See application file for complete search history.

(56) References Cited

U.S. PATENT DOCUMENTS

| | | | | |
|---|---|---|---|---|
| 3,522,253 | A * | 7/1970 | Little, Jr. et al. | 544/221 |
| 3,882,083 | A * | 5/1975 | Berger et al. | 528/15 |
| 3,892,643 | A * | 7/1975 | Tanaka et al. | 522/167 |
| 4,374,986 | A * | 2/1983 | Renner et al. | 544/221 |
| 5,101,029 | A * | 3/1992 | Stapp et al. | 544/221 |
| 5,106,933 | A * | 4/1992 | Kobayashi et al. | 528/15 |
| 5,204,408 | A * | 4/1993 | Konno et al. | 525/105 |
| 7,008,697 | B2 * | 3/2006 | Aketa et al. | 428/447 |
| 7,153,583 | B2 * | 12/2006 | Azechi et al. | 428/447 |
| 7,498,085 | B2 * | 3/2009 | Kashiwagi et al. | 428/447 |
| 2007/0100043 | A1 * | 5/2007 | Shiono | 524/261 |

FOREIGN PATENT DOCUMENTS

| | | |
|---|---|---|
| EP | 0 803 529 A1 | 10/1997 |
| JP | 9-291214 A | 11/1997 |
| JP | 2006-291044 A | 10/2006 |
| JP | 2007-9041 A | 1/2007 |
| JP | 4073223 B2 | 4/2008 |
| JP | 2008-143954 A | 6/2008 |
| JP | 2008-150506 A | 7/2008 |

* cited by examiner

*Primary Examiner* — Robert Loewe
(74) *Attorney, Agent, or Firm* — Birch, Stewart, Kolasch & Birch, LLP

(57) ABSTRACT

The purpose of the present invention is to provide an isocyanuric ring-containing organopolysiloxane which can provide a cured product which can exploit the properties of a hydrosilylation (addition reaction), and is suitable for use in an encapsulating materials for an optical semiconductor. Thus, the present invention provides an organopolysiloxane having at least one isocyanuric ring in a molecule and vinyl siloxy groups at both terminals, and represented by the following formula (1):

wherein X is, independently of each other, a monovalent organic group which does not have an unsaturated bond, $R^1$ and $R^2$ are, independently of each other, a methyl group or a phenyl group, and P is an integer of from 1 to 30.

3 Claims, 2 Drawing Sheets

ISOCYANURIC RING-CONTAINING POLYSILOXANE HAVING VINYL GROUPS AT THE TERMINALS

CROSS REFERENCE

This application claims the benefits of Japanese Patent Application No. 2009-253318 filed on Nov. 4, 2009, and Japanese Patent Application No. 2010-225825 filed on Oct. 5, 2010, the contents of which are herein incorporated by reference.

FIELD OF THE INVENTION

The present invention relates to an isocyanuric ring-containing organopolysiloxane which has vinyl siloxy groups at the both terminals and yields a cured product having excellent heat resistance, mechanical strength and electrical properties such as electrical insulation; gas permeabilities such as low moisture permeability; optical properties such as transparency; chemical resistance and water resistance.

BACKGROUND OF THE INVENTION

Curable silicone rubber compositions to be cured by a curing addition reaction are well known. These curable silicone rubber compositions have good weather resistance, heat resistance, and electrical insulation and, therefore, used as a molding material for electric and electronic parts such as a gasket material, potting material, a coating material, a roll material and a casting material; a wire-covering material and an automobile part. Additionally, they are used as an encapsulating material and an adhesive material for an optical semiconductor on account of their optical property.

The curable silicone rubber compositions have siloxane bonds which are inherent in a silicone and, therefore, cannot sometimes exert the excellent properties of silicones such as chemical resistance, water-proof property and gas permeability due to the ion binding property of the siloxane bonds in extremely severe environments such as hot and humid environments. The surface of the cured products obtained from the curable silicone rubber compositions has tacking which cause problems such as sticking of dust. Further, the polymer having siloxane bonds has good gas permeability and used as an oxygen enrichment membrane. However, when this is used as an encapsulating material for an optical semiconductor, the moisture permeability is detrimental.

Various kinds of polymers and encapsulating materials which contain an isocyanuric ring are known. Japanese Patent Application Laid-Open No. 2008-143954 (Patent Literature 1) describes a cured product prepared by an epoxide ring-opening reaction of an isocyanuric ring-containing polysiloxane which is prepared by an addition reaction of an SiH-containing polysiloxane with diallyl monoglycidyl isocyanurate. Japanese Patent Application Laid-Open No. 2008-150506 (Patent Literature 2) describes a cured product which is prepared by an addition reaction of an isocyanuric ring-containing polysiloxane with an SiH-containing polysiloxane. Japanese Patent Application Laid-Open No. Hei 9-291214 (Patent Literature 3) describes a cured product which is prepared by an addition reaction of a triallylisocyanurate with an SiH-containing polysiloxane. Japanese Patent No. 4073223 (Patent Literature 4), Japanese Patent Application Laid-Open No. 2006-291044 (Patent Literature 5) and Japanese Patent Application Laid-Open No. 2007-9041 (Patent Literature 6) describe a cured product which are prepared by an addition reaction of a polysiloxane which has an isocyanuric ring and an SiH group with an alkenyl group-containing compound.

However, the isocyanuric ring-containing polymer described in Patent Literatures 1 and 2 has siloxane bonds in the main chain and, therefore, flexible, but less compatible with a cross-linking agent. Further, the position of the alkenyl group in the isocyanuric ring-containing polymer is various, and thereby difficult to cure by an addition reaction. Therefore, a characteristic of a hydrosilylation (addition reaction), such as rapid curing reaction, is not exerted. The isocyanuric ring-containing polymers described in Patent Literatures 3 to 6 have high crosslink density, are rigid and have poor flexibility.

There has not been known any cured product which is prepared by an addition reaction of an isocyanuric ring-containing polysiloxane with an SiH group-containing polysiloxane, and which has good flexibility, curing property, compatibility, and optical property and low moisture permeability.

Patent Literature 1: Japanese Patent Application Laid-Open No. 2008-143954
Patent Literature 2: Japanese Patent Application Laid-Open No. 2008-150506
Patent Literature 3: Japanese Patent Application Laid-Open No. Hei-9-291214
Patent Literature 4: Japanese Patent No. 4073223
Patent Literature 5: Japanese Patent Application Laid-Open No. 2006-291044
Patent Literature 6: Japanese Patent Application Laid-Open No. 2007-9041

SUMMARY OF THE INVENTION

Problems to be Solved by the Invention

The purpose of the present invention is to provide an isocyanuric ring-containing organopolysiloxane which provide a cured product, taking advantage of the properties of a hydrosilylation (addition reaction), and is suitable for use in encapsulating materials for optical semiconductors. To solve the above-described problems, the present inventors have made research to find that an organopolysiloxane represented by the following formula (1) can provide a cured product which is superior in the above-described properties.

Means to Solve the Problems

Thus, the present invention provides an organopolysiloxane having at least one isocyanuric ring in a molecule and vinyl siloxy groups at both terminals, and represented by the following formula (1):

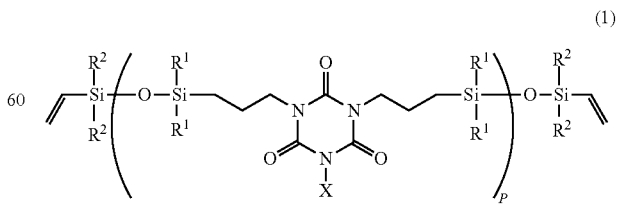

wherein X is, independently of each other, a monovalent organic group which does not have an unsaturated bond, $R^1$ and R² are, independently of each other, a methyl group or a phenyl group, and P is an integer of from 1 to 30.

BRIEF DESCRIPTION ON THE DRAWINGS

BEST MODES OF THE INVENTION

Figure 1:
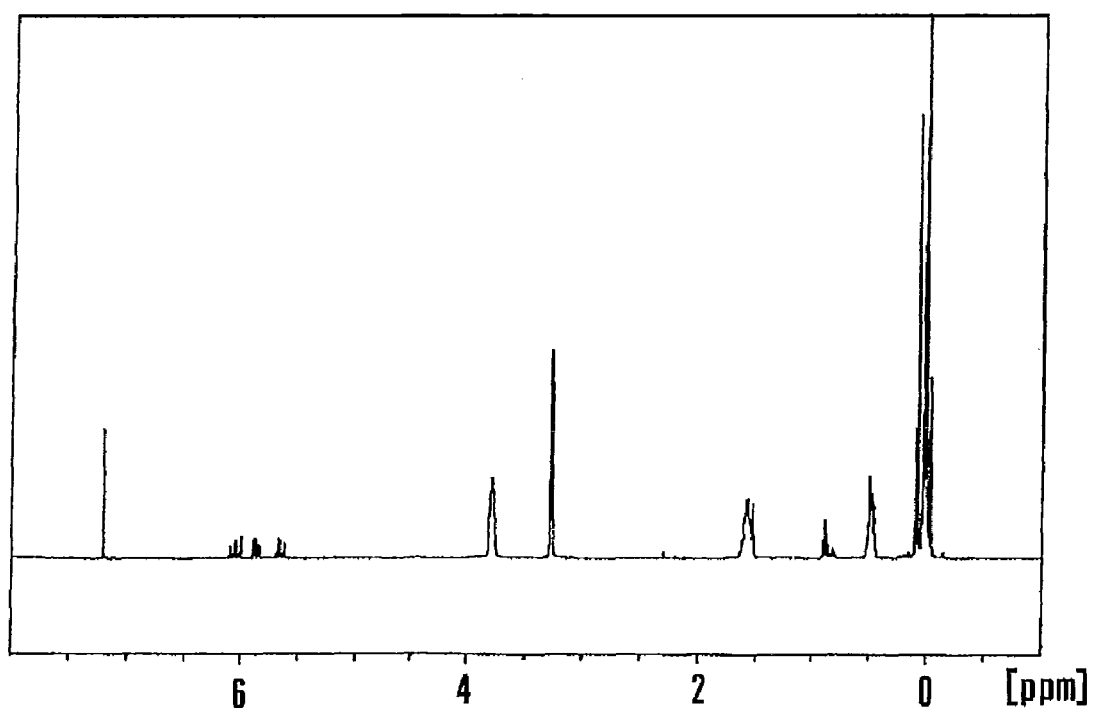
FIG. 1 is a chart of ¹H-NMR spectra of the compound 1 prepared in Example 1.

The organopolysiloxane of the present invention has the isocyanuric ring-containing structure represented by formula (1) and has vinylsiloxy groups in the both terminals.

In the formula (1), $R^1$ and $R^2$ are, independently of each other, a methyl group or a phenyl group, and preferably is a methyl group in view of a curing property, flexibility and easy synthesis of the composition. More preferably, 50 mole % or more of $R^1$ and $R^2$ are a methyl group.

X is, independently of each other, a monovalent organic group which does not have an unsaturated bond. Examples of X include alkyl groups and aryl groups. Preferably, X is an alkyl group having 1 to 4 carbon atoms, more preferably a methyl group.

P is an integer of from 1 to 30, preferably from 1 to 10.

A weight average molecular weight of the organopolysiloxane is preferably from 500 to 10,000, more preferably from 600 to 5,000, and most preferably from 1,000 to 3,000.

A viscosity at 25 degrees C. of the organopolysiloxane is preferably 0.1 to 100 Pa·s, more preferably 0.5 to 10 Pa·s.

The oraganopolysiloxane of the present invention can be prepared in the following method.

First, diallyl isocyanurate represented by the following formula (2) is addition reacted with alkoxysilane represented by the following formula (3) to prepare an intermediate represented by the following formula (4). The addition reaction may be performed according to any known procedures. A reaction temperature is 50 to 120 degrees C., preferably 70 to 100 degrees C. A reaction time is 0.1 to 24 hours, preferably 8 to 16 hours.

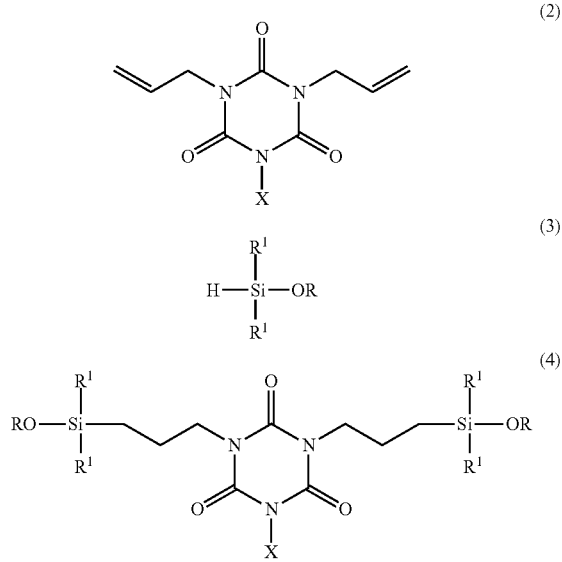

In the above-described formulas (2) to (4), $R^1$ and X are as defined above, R is alkyl group having 1 to 6 carbon atoms, a methyl, ethyl or propyl group.

The alkoxysilane represented by formula (3) may be added in a ratio of from 1 to 5 equivalents, preferably from 2 to 4 equivalents, of the SiH group per equivalent of the allyl group of the diallyl isocyanurate represented by formula (2).

In the addition reaction of the diallyl isocyanurate represented by formula (2) with the alkoxysilane represented by formula (3), a compound which comprises platinum, rhodium or palladium may be used as a catalyst. Preferred is a compound which comprises platinum, such as hexachloroplatinate (IV) hexahydrate, platinum carbonyl vinyl methyl complex, platinum-divinyltetramethyldisiloxane complex, platinum-eye lovinylmethylsiloxane complex, platinum-octylaldehyde/octanol complex and platinum supported on activated coal. The catalyst is added preferably in such an amount that the amount of the metal is from 0.01 to 10,000 ppm, more preferably from 0.1 to 100 ppm, relative to the amount of the compound represented by the formula (2).

Next, the intermediate represented by formula (4) and a terminal vinyl-modified organosiloxane represented by the following formula (5) are subjected to an equilibrating reaction. By the equilibrating reaction, the intermediate represented by formula (4) is polymerized to become an isocyanuric ring-containing organopolysiloxane, and a vinyl siloxy group is introduced into the both terminals of the isocyanuric ring-containing organopolysiloxane. The equilibrating reaction may be performed according to any known procedures. A reaction temperature is from room temperature to 250 degrees C., preferably of from 50 to 180 degrees C. A reaction time 0.1 to 120 hours, preferably is 1 to 10 hours.

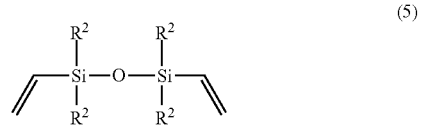

wherein, $R^2$ is as defined above.

The equilibrating reaction is carried out with a strong acid as a catalyst. Any known catalyst can be used, for example, protonic acids such as hydrochloric acid, sulfuric acid, trifluoroacetic acid, and trifluoromethanesulfonic acid; lewis acids such as iron chloride, aluminum chloride, zinc chloride, and titanium chloride, but are not limited to these. The amount of the catalyst to be used depends the acid strength of the catalyst. For instance, when sulfuric acid is used, approximately 1,000 to 100,000 ppm, preferably 5,000 to 50,000 ppm, of a sulfuric acid may be used, relative to a total weight of the compounds represented by the formula (4) and (5).

In the equilibrating reaction, 0.1 to 100 moles, preferably 0.5 to 30 moles, more preferably 1 to 10 moles, of the intermediate represented by formula (4) may be used, per mole of the siloxane represented by the formula (5), to obtain the isocyanuric ring-containing organopolysiloxane of the present invention. After the end of the reaction, any remaining terminal vinyl-modified organosiloxane can be removed by distillation under reduced pressure.

In the production of the present organopolysiloxane, a solvent may be added in the reaction mixture, if needed. The solvent may be toluene, xylene, mesitylene, diethylbenzene, tetrahydrofuran, diethyl ether, 1,4-dioxane, and diphenyl ether.

An Example of the present organopolysiloxane is represented by the following formula;

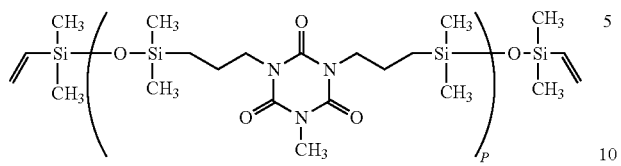

wherein P is as defined above.

The isocyanuric ring-containing organopolysiloxane of the present invention is reacted with a compound having an SiH group to provide a cured product which has superior mechanical property, heat resistance, electrical insulation, chemical resistance, water resistance, gas permeability, and optical properties. The cured product obtained is suitable as optical materials such as lenses and encapsulating materials for LED, which require transparency, and especially as encapsulating materials for semiconductors.

EXAMPLE

The present invention will be explained in detail by the reference to the Example, but shall not be limited thereto.

The measuring apparatuses used in the Example are as follows.
NMR: JMN LA-300WB, produced by JEOL, $^1$H-NMR
GPC: SC-8020, produced by TOSO Co., Ltd., and
Rotational viscometer: BM type at 25 degrees C.

Example 1

In a one-litter separable flask added were 200 g of monomethyl diallyl isocyanurate (0.896 moles) and 300 g of toluene, heated to 60 degrees C., to which 1 g of a solution of chloroplatinic acid in toluene containing 0.5% by weight of platinum was added dropwise, and then 280 g of dimethylethoxysilane (2.69 moles) was added dropwise (molar ratio of the Si—H group/the vinyl group was 1.5/1). The reaction mixture was stirred at 60 degrees C. for 12 hours, and toluene was distillated off under reduced pressure to obtain a colorless and transparent liquid.

The product obtained was analyzed by $^1$H-NMR and was found to be a compound represented by the following formula:

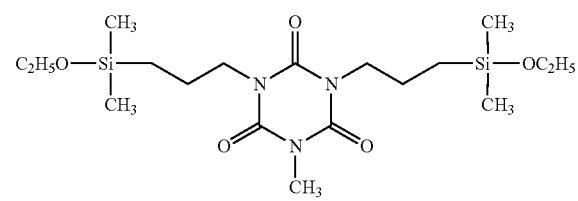

The viscosity at 25 degrees C. was 0.3 Pa·s.

In a 500-milliliter separable flask added were 100 g of the compound represented by the above-described formula (6) (0.248 moles), 46 g of vinylsiloxane represented by the following formula (7) (0.248 moles), and 18 g of water, to which 6 g of sulfuric acid was added dropwise. The reaction mixture was stirred at room temperature for 3 hours, washed with water and subjected to distillation under reduced pressure to obtain a colorless and transparent liquid.

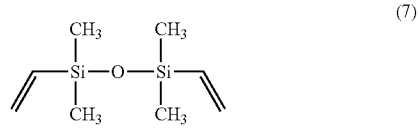

The product obtained was analyzed by $^1$H-NMR and GPC, and was found to be a compound represented by the following formula:

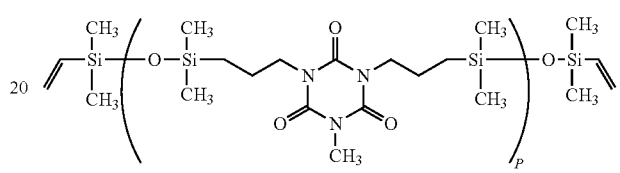

Figure 2:
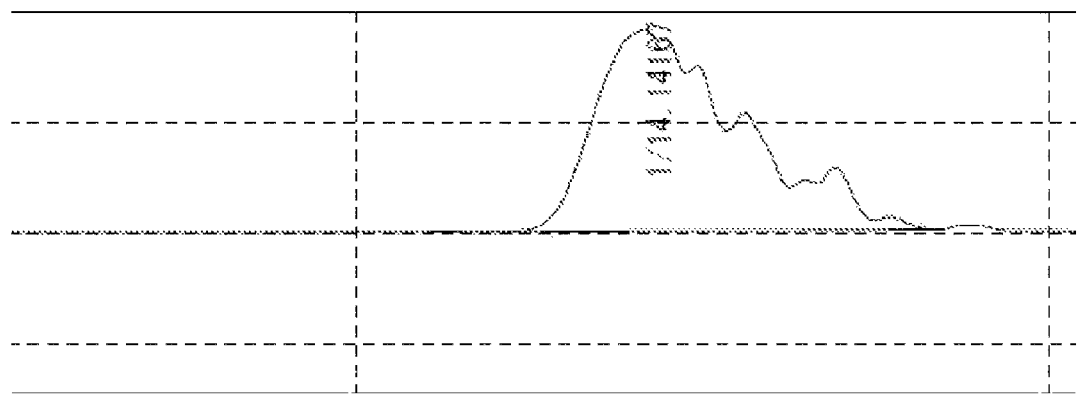
FIG. 2 is a chart of GPC spectra of the compound 1 prepared in Example 1.

The weight-average molecular weight was 1334 (average of P was 3.21). The $^1$H-NMR spectra are as shown in FIG. 1 and the GPC spectra are as shown in FIG. 2.

INDUSTRIAL APPLICABILITY

The isocyanuric ring-containing organopolysiloxane of the present invention is reacted with a compound having an SiH group to provide a cured product which has superior mechanical property, heat resistance, electrical insulation, chemical resistance, water resistance, gas permeability, and optical properties. The cured product obtained from the present organopolysiloxane is suitable as optical materials such as lenses material and encapsulating materials for a LED, which require transparency, and especially as encapsulating materials for semiconductors.

The invention claimed is:

1. An organopolysiloxane having at least one isocyanuric ring in a molecule and vinyl siloxy groups at both terminals, and represented by the following formula (1):

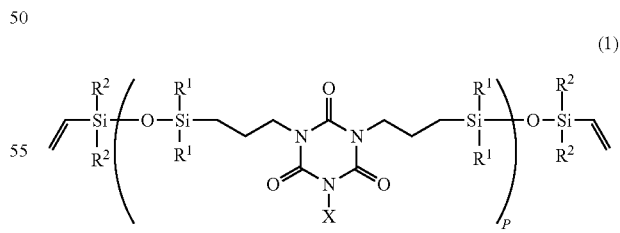

wherein X is, independently of each other, a monovalent organic group which does not have an unsaturated bond, $R^1$ and $R^2$ are, independently of each other, a methyl group or a phenyl group, and P is an integer of from 1 to 30.

2. The organopolysiloxane according to claim 1, wherein X is an alkyl group having 1 to 4 carbon atoms.

3. A method for preparing the organopolysiloxane according to claim 1 or 2, wherein a compound represented by the following formula (4) is reacted with a compound represented by the following formula (5):

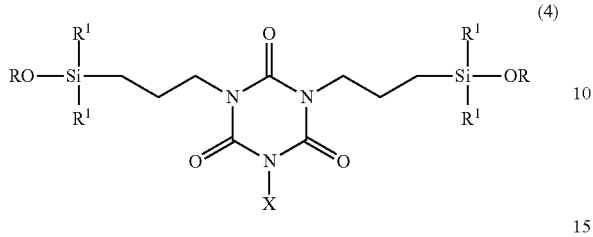
(4)

wherein X is, independently of each other, a monovalent organic group which does not have an unsaturated bond, $R^1$ is, independently of each other, a methyl group or a phenyl group, and R is an alkyl group having 1 to 6 carbon atoms,

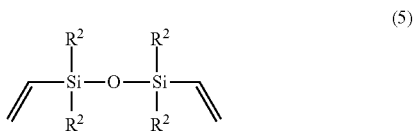
(5)

wherein $R^2$ is, independently of each other, a methyl group or a phenyl group.

* * * * *